United States Patent [19]

Ratti

[11] Patent Number: 4,837,317

[45] Date of Patent: Jun. 6, 1989

[54] PROCESS FOR THE PREPARATION OF 6-[D(—)ALPHA-(4-ETHYL-2,3-DIOXOPIPER-AZIN-1-YLCARBONYLAMINO)-ALPHA-PHENYLACETAMIDO]-PENICILLANIC ACID AND INTERMEDIATES USEFUL IN THIS PROCESS

[75] Inventor: Luigi Ratti, Bergamo, Italy

[73] Assignee: Biochimica Opos S.p.A., Milan, Italy

[21] Appl. No.: 105,097

[22] Filed: Oct. 5, 1987

[30] Foreign Application Priority Data

Oct. 6, 1986 [IT] Italy .................................. 21913 A/86

[51] Int. Cl.$^4$ ................... C07D 499/12; C07D 417/10; C07D 277/68
[52] U.S. Cl. ..................................... 540/316; 540/333; 544/369; 548/172
[58] Field of Search ................ 540/316, 333; 544/369; 548/172

[56] References Cited

U.S. PATENT DOCUMENTS 4,610,822  9/1986  Boop et al. .......................... 540/316

Primary Examiner—Werren B. Lone
Assistant Examiner—Vera C. Clarke
Attorney, Agent, or Firm—Michael N. Meller

[57] ABSTRACT

The 6-[D(—)-alpha(4-ethyl-2,3-dioxopiperazin-1-ylcarbonylamino)-alphaphenylacetamido]penicillanic acid and the salts thereof are prepared by synthetizing the novel intermediates, thioesters of D(—)-alpha-(4-ethyl-2,3-dioxopiperazin-1-ylcarbonylamino)-alpha-phenylacetic acid, with mercaptoheterocycles and by converting them into the desired compound by reaction with 6-amino-penicillanic acid.

8 Claims, No Drawings

PROCESS FOR THE PREPARATION OF 6-[D(—)ALPHA-(4-ETHYL-2,3-DIOXOPIPERAZIN-1-YLCARBONYLAMINO)-ALPHA-PHENYLACETAMIDO]-PENICILLANIC ACID AND INTERMEDIATES USEFUL IN THIS PROCESS

The present invention relates to a process for the preparation of 6-[D(-)-alpha-(4-ethyl-2,3-dioxopiperazin-1-ylcarbonylamino)-alpha-phenyl-acetamido]-penicillanic acid and of the salts thereof as well as novel intermediates useful in said process. The 6-[D(-)-alpha-(4-ethyl-2,3-dioxopiperazin-1-ylcarbonylamino)-alpha-phenylacetamido]penicillanic acid is a semisynthetic penicillin useful in the treatment of bacterial infections especially due to microorganisms of the pseudomonas strain.

It has been given the international common denomination "piperacillin" and with such a name it will be indicated in the present specification. The sodium salt thereof will be indicated as "sodium piperacillin". The piperacilline is disclosed and claimed in the US Pat. No. 4087424 and processes for the preparation thereof are furthermore described for instance in the Japanese Laid Open Patent Applications Nos. 53-10076, 53-20996 and 60-50796.

However, according to the processes of the above patents, it is necessary to protect the carboxylic group of the 6-aminopenicillanic acid for example through a silylation technique.

It has been now found that the piperacillin and the salts thereof, such as the salt, with alkali metals, preferably as sodium salt, can be obtained by a very simplified method, without any protection of the carboxylic group of the 6-aminopenicillanic acid, by using, as intermediate, a suitable thioester of D(-)-alpha-(4-ethyl-2,3-diox-opiperazina-1-ylcarbonylamino)-alpha-phenylacetic acid. Such an intermediate does react with a salt of the 6-aminopenycillanic acid to give piperacillin with optimum yields.

Thus, the present invention relates, according to a first aspect, to a process for the preparation of piperacillin, as represented by the formula:

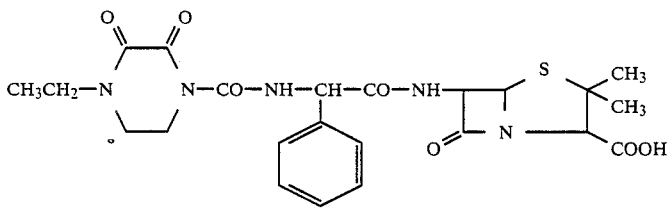

(I)

and of the pharmaceutically acceptable salts thereof, characterized in that:
(a) a functional derivative of D(-)-phenylglycine is reacted in an organic
 group

representing 5 or 6 membered heterocycle which may contain a further heteroatom which can be substituted or fused with a possibly substituted benzene ring;

(b) the thioester of D(-)-phenylglycine thus obtained having formula:

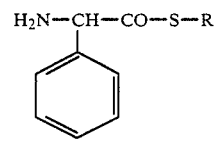

wherein R has the above meaning, is reacted with N-(4-ethyl-2,3-dio-xopiperazin-1-ylcarbonyloxy)succinimide having the formula:

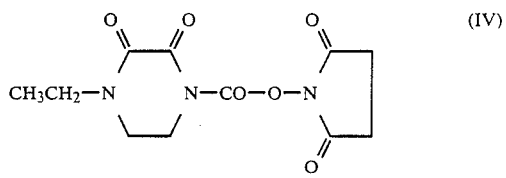

in an organic solvent;
(c) the thioester of D(-)alpha-(4-ethyl-2,3-dioxopiperazin-1-ylcarbonylamino)-alpha-phenylacetic acid of formula:

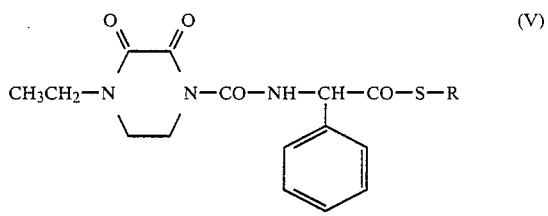

wherein R has the above defined meaning, is reacted with 6-aminopenicillanic acid or a salt thereof in an organic solvent at a temperature of between $-40°$ C. and $-5°$ C.; and if necessary the thus obtained product is converted into a pharmaceutically acceptable salt thereof.

The functional derivative of D(-)-phenylglycine used as the starting product in the process of the present invention can be one of the compounds of common use in the synthesis of penicillines and of peptides, such as anhydride, the same acid activated for instance with dicyclohexilcarbodiimide, an active ester such as 4-nitrophenylic ester, a halide, for example the chloride under the form of hydrochloride, a mixed anhydride for instance with carbonic acid monoethyl ester and the like.

The mercaptoheretocycle used as the reactant in the step (a) has the formula R-SH, wherein R represents a 5 or 6 membered heterocycle which may contain another heteroatom such as oxygen, nitrogen, or sulfur and which can be substituted or fused with a possibly substituted benzene ring.

Preferably R represents a 2-benzothiazolyl group.

The mercaptoheterocycle of formula II can be used as such or by preparing it in situ from the corresponding bisulfide of formula R—S—S—R (IIa) wherein R is as above defined.

Thus the step (a) can be carried out by reacting the functional derivative of D(-)-phenylglycine, preferably the hydrochloride of the chloride thereof, with a compound of formula R-SH, wherein R is as above defined, preferably a 2-benzothiazolyl group, in a polar aprotic solvent, such as N,N-dimethylformamide, N,N-dimethylacetamide, dimethylsulfoxide and the like. However other aprotic solvents, such a methyl chloride or acetonitrile, can be advantageously used.

According to a variation, the step (a) can be carried out by reacting the functional derivative of D(-)-phenylglycine preferably the hydrochloride of the chloride thereof, with a compound of formula R—S—S—R—, wherein R is as above defined.

The reaction is preferably carried out in the presence of a triakyl phosphine, a triarylphospine, a trialchilphosphite or a triarylphosphite, preferably triethylphosphite or triphenylphosphine, and also in the presence of a tertiary amine such as triethylamine or N-methylmorpholine. As the sovlent there is generally used a polar aprotic solvent as above exemplified or another aprotic solvent such as methyl chloride, chloroform or acetonitrile.

The thioester of D(-)-phenylglycine of formula III thus obtained is isolated with high yields according to standard methods, for example through precipitation in a suitable solvent; the preferred thioester is that with 2-mercaptobenzothiazole.

The step (b) is carried out by reacting the thioester of D(-)-phenylglycine of formula III obtained at the end of the step (a) with N-(4-ethyl-2,3-dioxopiperazin-1-ylcarbonyloxy)-succinimide of formula IV in an organic solvent such as dibutylether, 1,2-dimethoxyethane, dioxane, tethrahydrofuran and the like.

The thioester of D(-)-alpha-(4-ethyl-2,3-dioxopiperazin-1-ylcarbonylamine) phenylacetic acid of formula V thus obtained is isolated with high yields according to standard methods, for example by removing the reaction by products at a slightly alkaline pH and by evaporating the solvent.

The preferred thioester is that with 2-mercaptobenzothiazole.

The compound of formula IV used as the reactant in the step (b) is known from the literature;it can be readily obtained with 80-100% yields by reacting the reaction product between 4-ethyl-2,3-dioxopiperazine and phosgene or ethylchlorocarbonate with N-hydroxy succinimide in pyridine.

The step (c) is carried out by reacting the thioester of D(-)-alpha-(4-ethyl)-2,3-dioxopiperazin-1-ylcarbonylamino)-alpha-phe acid of formula V, preferably the thioester with 2,3-mercaptobenzothiazole, and the 6-aminopenicillanic acid, preferably as one of its salts, in a polar aprotic solvent, such as N,N-dimetylformamide, N,N-dimethylacetamide, dimetylsulphoxide and like or in another aprotic solvent at the temperature of between $-40°$ C. and $+5°$ C.

The thus obtained piperacillin is isolated with a yield of 75 to 90% according to the standard techinques, for instance by acidification, extraction with a suitable solvent and evaporation of said solvent.

The piperacillin in form of free acid can be converted into one of its pharmaceutically acceptable salts according to known methods.

For instance, the preferred salt thereof, the sodium piperacillin, is obtained by reaction with sodium ethylhexanoate and crystallization in order to obtain a crystalline product.

Alternatively the piperacillin, as obtained at the end of the step (c), is suspended in water, then an aqueous solution of sodium bicarbonate is added to said suspension up to a pH of 5.2-5.3 and the thus obtained solution is lyophilized under sterile conditions and the powder is filled into vials ready for the therapeutical use.

The process of the present invention is of very easy carrying out. The several reactions, apart from the step (c), can be carried out at room temperature (about $20°-25°$ C.) and do not require particular care such as the protection of sensible groups.

The yield of final product is fully satifactory and at least equal to that which is obtained according to the know processes.

The above compounds III and V are novel and represent useful intermediates in the process of the present invention.

Consequently according to another feature, the present invention relates to novel thioesters of formula:

$$X-NH-CH-CO-S-R \quad\quad VI$$
$$|$$
$$\text{(phenyl)}$$

wherein X represents hydrogen or a group;

$$CH_3CH_2-N\underset{\diagdown\_\_\diagup}{\overset{O\diagdown\quad\diagup O}{\diagup N}}-CO-$$

and R has the above defined meaning, but preferbly is 2-benzothiazolyl. The following examples illustrated invention without however limiting it.

PREPARATION

A suspension of 0.04 moles of 1-(4-ethyl-2,3-dioxopiperazin-1-yl)carbonyl chloride in a solution of 0.04 moles of N-hydroxysuccinimide in 30 ml of pyridine is mantained under stirring for 15 hours at room temperature ($20°-25°$ C.). The solution is then evaporated under reduced pressure and the residue is taken with 50 ml of chloroform and 25 ml of water; the chloroform phase is separated, washed with 25 ml of water, dried onto anhydrous magnesium sulphate and evaporated under reduced pressure. There is thus obtained N-(4-ethyl-2,3-dioxopyperazidin-1-ylcarbonyloxysuccinimide in form of oil.

Analysis for $C_{11}H_{13R}N_3O_6$ (M.W. 283.246)
Calculated % C 46.64—H 4.63—N 14.83
Found % C 46.77—H 4.58—N 14.78

EXAMPLE 1

A solution of 0.08 moles of 2-mercaptobenzothiazole in 40 ml of N,N-dimethylformamide is added with 0.72 moles of D(-)phenylglycine chloride hydrochloride, whereby the temperature increases up to 38° C. The mixture is left to spontaneously return to the room temperature (20°-25° C.), then is maintained for 4 hours at the same temperature. The mixture is poured into 185 ml of ethyl ether and the thus formed crystalline product is separated by filtration. There is thus obtained the thioester of D(-)-phenylglycine with 2-mercaptobenzothiazole (formula VI, X=H R=2-benzothiazolyl).

EXAMPLE 2

A solution of 0.15 moles of the thioester of D(-)-phenylglycine with 2-mercaptobenzothiazole in 80 ml of 1,2-dimethoxyethane is added with 0.18 moles of N-(4-ethyl-2,3-dioxopiperazin-1-ylcarbonyloxy)succinimide. The pH of the mixture is brought to about 8 by adding Amberlite IR-45 ® and the thus obtained suspension is stirred for 2 hours at 20°-25° C. The resin is removed by filtration and the pH of the solution is brought to 7 by adding a solution of hydrogen chloride in 1.2-dimethoxyethane. The solution is evaporated under reduced pressure up to a volume of about 20 ml, then isopropanol is added and the desired product is crystallized. There is thus obtained the thioester of D(-)-alpha-(4-ethyl-2,3-dioxopiperazin-1-ylcarbonylamino)-alpha-phenylacetic acid with 2-mercaptobenzothiazole (formula VI- X=

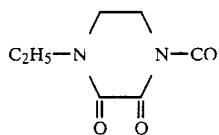

R=2-benzothiazolyl) with a yield of 75%; m.p. 135°-140° C. (dec.)

Analysis for C$_{22}$H$_{20}$N$_4$O$_4$S (M.W. 436.494)
Calculated %=C 60.54—H 4.62—N 12.83—S 7.35
Found % =C 60.59—H 4.70—N 12.88—S.7.29

EXAMPLE 3

A solution of 0.02 moles of the salt of triethylamine of the 6-aminopenicillanic acid in 120 ml of N,N-dimethylformamide is added with 0.022 moles of the thioester of D-(-)-alpha-(4-ethyl-2,3-dioxopiperazinl-ylcarbonylamino)-alpha-phenylacetic acid with 2-mercaptobenzothiazole, under stirring and at a temperature between −15° C. and −20° C. The stirring is continued for 20 minutes, then the reaction mixture is diluted with 280 ml of water and the pH is brought to 2-2,2 by adding 37% hydrochloric acid. The product which is separated is extracted with 220 ml of ethylacetate, the layer of ethyl acetate is collected, washed with a 20% aqueous solution of sodium chloride, then with water and lastly it is dried onto anhydrous sodium sulphate. The thus obtained solution is evaporated under reduced pressure up to a volume about 80 ml. The product is crystallized and, after 3 hours at 5° C., it is filtered, washed with ethylacetate and dried at 45° C. under reduced pressure.

The pure pyperacilli is thus obtained; m.p. 183°-85° C. (dec.) The product is identical to an authentic sample.

EXAMPLE 4

A suspension of 0.01 moles of piperacillin in water is added with an aqueous solution of sodium bicarbonate up to a pH of 5.2-5.3.

The thus obtained solution is lyophilized and there is obtained sodium piperacillin for therapeutical use.

What is claimed:

1. A process for the preparation of 6-D-(-)-alpha-4-(ethyl-2,3-dioxopiperazin-1-ylcarbonylamino)-alpha-phenyl-acetamido penicillanic acid of formula:

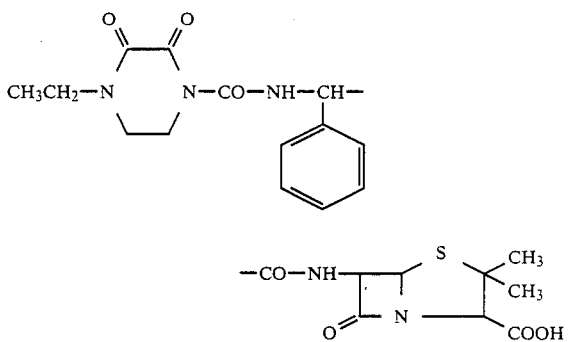

and of the pharmaceutically acceptable salts thereof, characterized in that:

(a) a functional derivative of D(-)-phenylglycine is reacted in an organic solvent with a mercaptoheterocycle of formula R—SH (II), wherein R—SH is a mercaptobenzothiazole;

(b) the thioester of D(-)-phenylglycine thus obtained having formula:

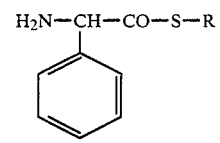

wherein R is a benzothiazolyl group, is reacted with N-(4-ethyl-2,3-dioxopiperazin-1-ylcarbonyloxy) succinimide having the formula:

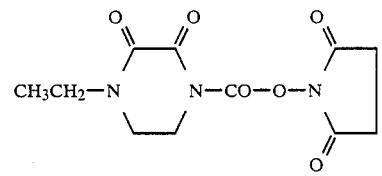

in an organic solvent;

(c) the thioester of D(-)alpha-(4-ethyl-2,3-dioxopiperzin-1-ylcarbonylamino)-alpha-phenylacetic acid of formula:

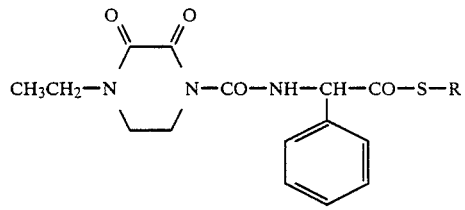

wherein R is as defined above, is reacted with 6-aminopenicillanic acid or a salt thereof in an organic solvent at a temperature of between −40° C. and −5° C.; and if necessary the thus obtained product is converted into a pharmaceutically acceptable salt thereof.

2. A process according to claim 1, characterized in that as the starting material for the step (a) there is used D(-)-phenylglycine chloride hydrochloride.

3. A process according to claim 1, characterized in that in the step (a), as mercaptoheterocycle there is used 2-mercaptobenzothiazole.

4. A process according to claim 1, characterized in that each step is carried out in a polar aprotic solvent.

5. A process according to claim 4, characterized in that said solvent is selected from the group consisting of N,N-dimethylformamide, N,N-dimethylacetamide, and dimethylsulfoxide .

6. A thioester of D(-)-phenylglycine of formula:

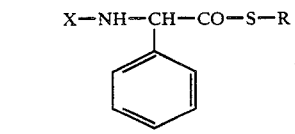

wherein X is hydrogen and R is a benzothiazolyl group.

7. A thioester of D(-)-phenylglycine with 2-mercaptobenzothiazole of formula

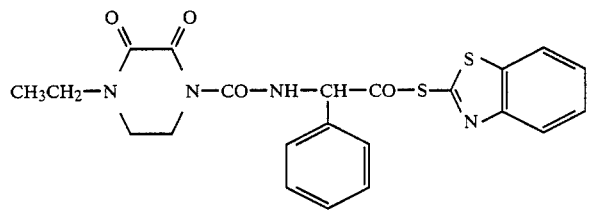

8. A thioester of D(-)-alpha-(4-ethyl-2,3-dioxopiperazin-1-ylcarbonylamino)-alpha-phenylacetic acid wtih 2-mercaptobenzothiazole of formula:

* * * * *